(12) United States Patent
Shao et al.

(10) Patent No.: US 8,925,481 B2
(45) Date of Patent: Jan. 6, 2015

(54) SYSTEMS AND METHODS FOR MEASURING, MONITORING AND CONTROLLING OZONE CONCENTRATION

(75) Inventors: ShouQian Shao, Fremont, CA (US); Jay DeDontney, Prunedale, CA (US); Jason Wright, Saratoga, CA (US)

(73) Assignee: Intermolecular, Inc., San Jose, CA (US)

( * ) Notice: Subject to any disclaimer, the term of this patent is extended or adjusted under 35 U.S.C. 154(b) by 533 days.

(21) Appl. No.: 13/271,449

(22) Filed: Oct. 12, 2011

(65) Prior Publication Data
US 2013/0092084 A1    Apr. 18, 2013

(51) Int. Cl.
    B05C 11/10    (2006.01)
    G01N 7/00    (2006.01)
    C23C 16/52    (2006.01)
    C23C 16/455    (2006.01)

(52) U.S. Cl.
    CPC ...... *C23C 16/52* (2013.01); *G01N 7/00* (2013.01); *C23C 16/45512* (2013.01); *C23C 16/45557* (2013.01)
    USPC ........................................ 118/663; 73/861.04

(58) Field of Classification Search
    CPC .............................. C23C 16/455; C23C 16/52
    USPC .......... 73/31.04, 861.04, 25.01; 118/663, 712
    See application file for complete search history.

(56) References Cited

U.S. PATENT DOCUMENTS

| | | | |
|---|---|---|---|
| 5,604,298 A * | 2/1997 | Dosoretz et al. ............... 73/23.2 |
| 5,904,170 A | 5/1999 | Harvey et al. |
| 6,857,324 B2 * | 2/2005 | Sato et al. .................. 73/861.61 |
| 7,757,541 B1 * | 7/2010 | Monkowski et al. .......... 73/1.34 |
| 2003/0049376 A1 * | 3/2003 | Schwarm et al. ........ 427/255.28 |
| 2003/0049390 A1 * | 3/2003 | Shanmugasundram et al. ............................. 118/715 |
| 2010/0119439 A1 | 5/2010 | Shindou |

* cited by examiner

*Primary Examiner* — Lisa Caputo
*Assistant Examiner* — Punam Roy (57) ABSTRACT

Systems and methods to determine ozone concentration in a gas mixture of ozone and oxygen, based on measurements of a total mass flow and a corresponding change in a chamber pressure accepting the mixture flow, can enable the measurements of ozone concentration at low pressure settings. The ozone concentration determination can be applied to a vacuum processing chamber, enabling precision semiconductor processing.

15 Claims, 11 Drawing Sheets

SYSTEMS AND METHODS FOR MEASURING, MONITORING AND CONTROLLING OZONE CONCENTRATION

FIELD OF THE INVENTION

The present invention relates generally to determining a concentration of a gas in a gas mixture flow, and particularly related to determining ozone concentration in a gas mixture where ozone is generated from oxygen gas.

BACKGROUND OF THE INVENTION

Ozone has been widely used in semiconductor processing. For example, ozone can be used in combination with TEOS to deposit silicon dioxide. Ozone can be used in atomic layer deposition (ALD) process to form oxide films, such as aluminum oxide or hafnium oxide. Ozone can also be used for cleaning semiconductor wafers and semiconductor equipment, especially for removing hydrocarbon residues.

In general, an ozone generator is located a distance from the processing chamber, with the ozone concentration is measured at the output of the ozone generator. However, process windows have become narrower in advanced applications of both front end of line (FEOL) and back end of line (BEOL), especially in ALD, chemical vapor deposition (CVD) and interface treatment, and the ozone settling time between the ozone generator and the process chamber can cause the ozone concentration at the process chamber to be different from the desired level, leading to a compromised semiconductor product.

Thus, monitoring, measuring or controlling the ozone concentration at the point of use becomes critical. This has imposed additional requirements on ozone-related equipment, such as ozone generator and ozone concentration sensors. For example, in most applications the ozone is fed into a chamber where the pressure is under or around a few Torr range. However, there is no ozone sensor available to measure ozone concentration at such low pressure. For example, the available ozone sensors in the market which use UV absorption method, can only measure the ozone concentration above 8 PSI (405 Torr).

Therefore, ozone concentration sensors and controllers capable of operating at low pressure are needed.

SUMMARY OF THE DESCRIPTION

The present invention relates to systems and methods to determine a concentration of a gas in a gas mixture flow, such as the concentration of ozone in a mixture of ozone and oxygen, or the concentration of oxygen in a mixture of oxygen and nitrogen. The determination is based on measurements of mass flow rates and pressures due to the gas mixture flow.

In some embodiments, the present invention discloses systems and methods to determine a concentration of a first gas generated from a converted portion of a second gas, forming a two-gas mixture comprising the first gas and the remaining portion of the second gas. The method comprises determining a mass flow rate of the second gas, and a corresponding pressure of the gas mixture, and then calculating the concentration of the first gas through a formula connecting these two values.

For example, to determine a concentration of ozone in a gas mixture of ozone and oxygen generated from an oxygen flow, a mass flow rate change of the oxygen flow and a pressure change of the gas mixture flow are measured. The two measured changes are related through the ideal gas law, permitting solving the equation to provide the concentration of ozone with respect to the gas mixture.

In some embodiments, the present invention discloses systems and methods to determine a concentration of a first gas in a multiple-gas mixture comprising the first gas, a second gas, and one or more third gases, comprising subtracting the effect of the third gases from the gas mixture, and then calculating the concentration of the first gas based on the mixture of two gases.

For example, to determine a concentration of ozone in a gas mixture of ozone, oxygen, and nitrogen, a change of the total flow rate comprising oxygen and nitrogen is measured. Since the nitrogen flow is known, the flow rate change of nitrogen can be subtracted from the total flow. Alternatively, a flow rate change of oxygen flow can be measured directly. The corresponding pressure change for only ozone and oxygen can be similarly calculated. The system is then equivalent to a two-gas mixture system, and the concentration of ozone can be calculated from the two-gas mixture formulation.

In some embodiments, the present invention discloses systems and methods for controlling a concentration using a measure concentration to control a generator until a desired concentration is achieved.

In some embodiments, the present invention discloses systems and methods to use an ozone concentration measurement system in a vacuum chamber system.

BRIEF DESCRIPTION OF THE DRAWINGS

To facilitate understanding, identical reference numerals have been used, where possible, to designate identical elements that are common to the figures. The drawings are not to scale and the relative dimensions of various elements in the drawings are depicted schematically and not necessarily to scale.

The techniques of the present invention can readily be understood by considering the following detailed description in conjunction with the accompanying drawings, in which.

DETAILED DESCRIPTION

A detailed description of one or more embodiments is provided below along with accompanying figures. The detailed description is provided in connection with such embodiments, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For the purpose of clarity, technical material that is known in the technical fields related to the embodiments has not been described in detail to avoid unnecessarily obscuring the description.

In some embodiments, the present invention discloses systems and methods to determine individual mass flow rates or concentration in a gas mixture from the data of the gas mixture. For example, by determining or measuring flow rate and pressure values due to the gas mixture, the present invention can provide individual flow rates or concentration of the gas components in the gas mixture. In some embodiments, the present methodology is based on the different characteristics of the individual gases in the gas mixture, which then enable the determination of the properties of the individual gases from the total gas mixture data. The gas mixture can be a mixture of two or more gases.

In some embodiments, the present invention discloses systems and methods to determine individual mass flow rates or concentration of a gas mixture generated from a supply gas. For example, an oxygen supply gas can produce a two-gas mixture of ozone and oxygen through an ozone generator, where ozone is generated from a converted portion of the oxygen supply gas and oxygen comprises the remaining portion. The following description describes the invention in the embodiments of ozone generated from oxygen, but the invention is not so limited, and can be applied to any gas mixture system.

Ozone can be generated using different generation methods such as corona discharge or ultraviolet light. Ozone concentration is calculated as the amount of ozone in the mixture of ozone and oxygen, expressed as a ratio of ozone and the mixture. Ozone concentration can be measured in µmol/mol (or ppm, parts per million)

$$C\left(\frac{\mu mol}{mol}\right) = \frac{\text{moles of ozone} \times 10^{-6}}{\text{moles of ozone} + \text{moles of oxygen}}$$

or weight percent (wt %)

$$C(\text{wt \%}) = \frac{\text{weight of ozone} \times 100}{\text{weight of ozone} + \text{weight of oxygen}}$$

The concentration of ozone typically ranges from 1 to 5 wt % in air and from 6 to 20 wt % in oxygen.

In an ozone generator, oxygen is converted to ozone as followed:

$$3O_2 + \text{Energy} \rightarrow 2O_3$$

Some catalyst can also be added to the generator, for example, a small amount of nitrogen can improve the efficiency of an ozone generator $$3O_2 + N_2 + \text{Energy} \rightarrow 2O_3 + N_2$$

In some embodiments, the present invention discloses determining an ozone concentration based on the change of the number of molecules when converted from oxygen to ozone. Specifically, three molecules of oxygen are needed to form two molecules of ozone. The mole change can affect the gas pressure, and thus a measurement of gas pressure can provide information about the numbers of moles, for example, through an ideal gas law:

$$PV = nRT$$

where P is the gas pressure, V is the gas volume, T is the gas temperature, n is the number of molecular moles, and R is the ideal gas constant (8.314 J K$^{-1}$ mol$^{-1}$).

When the gas is a mixture, for example, containing ozone and oxygen, the ideal gas law can be expressed as, where $n_{O2}$ and $n_{O3}$ are the numbers of moles of oxygen and ozone, respectively $$n_{O_2} + n_{O_3} = \frac{V}{RT}P \quad \text{(Eqn 1)}$$

Through a measurement of gas pressure, keeping volume and temperature constant, the total moles of ozone and oxygen in the gas mixture can be calculated.

The number of atoms in $n_{O3}$ moles of ozone would be 3*$n_{O3}$*Avogadro, and the number of atoms in $n_{O2}$ moles of oxygen would be 2*$n_{O2}$*Avogadro. Since ozone is generated from supply oxygen, conservation of atoms provides that the number of atoms in the supply oxygen flow $O_2^S$ is equal to the sum of oxygen atoms and ozone atoms in the generated mixture flow.

$$2n_{O_2}{}^S * \text{Avogadro} = 2n_{O_2} * \text{Avogadro} + 3n_{O_3} * \text{Avogadro}$$

or $$2n_{O_2}{}^S = 2n_{O_2} + 3n_{O_3}$$

Through a measurement of the supply oxygen gas flow, the total moles of supply oxygen gas can be determined, for example, by dividing the mass flow rate F of the supply oxygen to the molecular mass $M_{O2}$ of oxygen:

$$2n_{O_2^S} = 2\frac{F}{M_{O_2}} = 2n_{O_2} + 3n_{O_3} \quad \text{(Eqn 2)}$$

Equations 1 and 2 enable the determination of ozone and oxygen molecules in the gas mixture through measurements of gas mixture pressure P and gas mass flow F. Ozone concentration in wt % can be calculated using mass of oxygen $M_{O2}$ and mass of ozone $M_{O3}$ $$C(\text{wt \%}) = 100 \frac{n_{O_3} \times M_{O_3}}{n_{O_3} \times M_{O_3} + n_{O_2} \times M_2} \quad \text{(Eqn 3)}$$

Preferably, instead of absolute values, changes can be used in equations 1 and 2, relating pressure change $\Delta P$ and the corresponding amount of mass flow $\Delta F$ (or moles of oxygen $\Delta n_{O2}$ and ozone $\Delta n_{O3}$) during the pressure change. Ozone concentration can be calculated accordingly:

$$C(\text{wt \%}) = 100 \frac{\Delta n_{O_3} \times M_{O_3}}{\Delta n_{O_3} \times M_{O_3} + \Delta n_{O_2} \times M_{O_2}} \quad \text{(Eqn 4)}$$

or, as a function of $\Delta P$ and $\Delta F$ $$C(\text{wt \%}) = \frac{M_{O_3}\left(\Delta F - M_{O_2} \Delta P \frac{V}{RT}\right)}{\Delta F(M_{O_3} - M_{O_2})} \quad \text{(Eqn 5)}$$

Figure 1A:
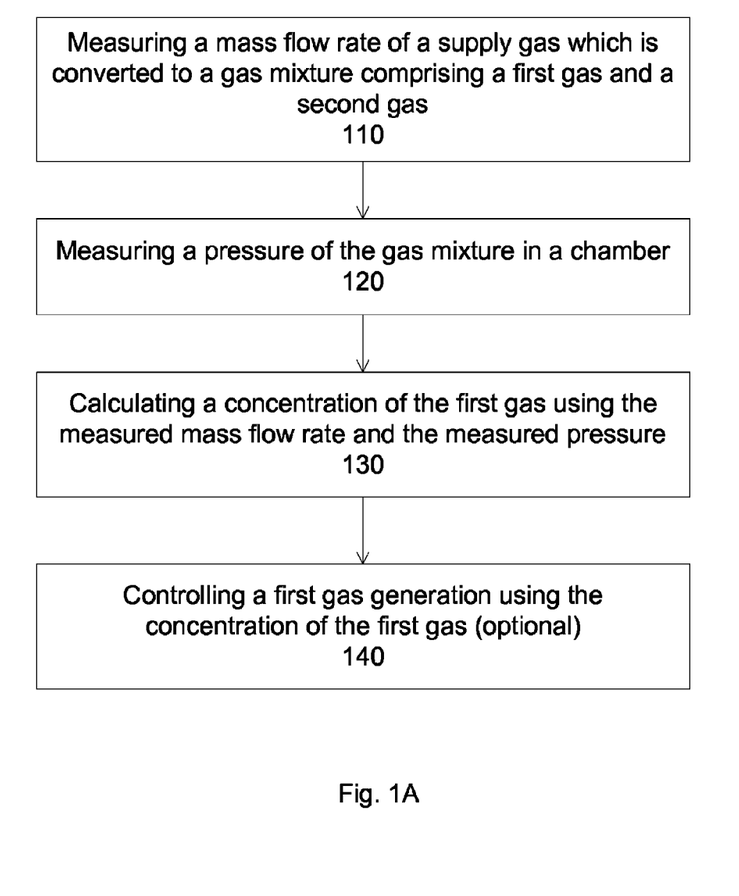
FIG. 1A illustrates an exemplary flowchart for determining individual mass flow rates or concentration in a gas mixture flow according to some embodiments of the present invention.

FIG. 1A illustrates an exemplary flowchart for determining individual mass flow rates or concentration in a gas mixture flow according to some embodiments of the present invention. By determining a mass flow rate of a supply gas which is converted to a gas mixture, together with a pressure in a chamber accepting the gas mixture, the flow rates of individual gases in the mixture, and consequently the mass concentration of an individual gas in the mixture, can be calculated.

In operation 110, a mass flow rate of a supply gas is measured. The gas mixture is generated from a supply gas, such as an oxygen supply gas generating a mixture of ozone and oxygen. Additional gases can be included in the gas mixture, such as a nitrogen catalyst for an ozone generator.

In some embodiments, the mass flow rate can be determined by measuring the flow rate of the supply gas, such as at an inlet of a generator system. For example, a mass flow meter or controller can be coupled to an oxygen supply gas which is supplied to an ozone generator.

In operation 120, the gas mixture is supplied to a chamber of known volume, and a chamber pressure is measured.

In operation 130, the individual mass flow rates or the concentration can be calculated using the mass flow rate and the measured chamber pressure.

Different methods to calculate the individual mass flow rates or the concentration are within the scope of the present invention. For example, the calculation can be based on the system of linear equations (Eqns 1 and 2), or any formula linking the concentration to the mass flow rate and the pressure (such as Eqn 3).

In some embodiments, the present invention discloses systems and methods to control a concentration, where the calculated concentration value can be used to achieve a desired concentration setting, for example, by adjusting a gas generation system according to the concentration reading. In operation 140, the concentration of the first gas can be used to control a first gas generation system to achieve a desired or a setting concentration value.

For example, the concentration measurement can be applied to an ozone/oxygen mixture where the ozone is generated from an ozone generator. To achieve a desired ozone concentration, the power of the ozone generator can be dynamically adjusted with feedback from the measured ozone concentration.

Figure 1B:
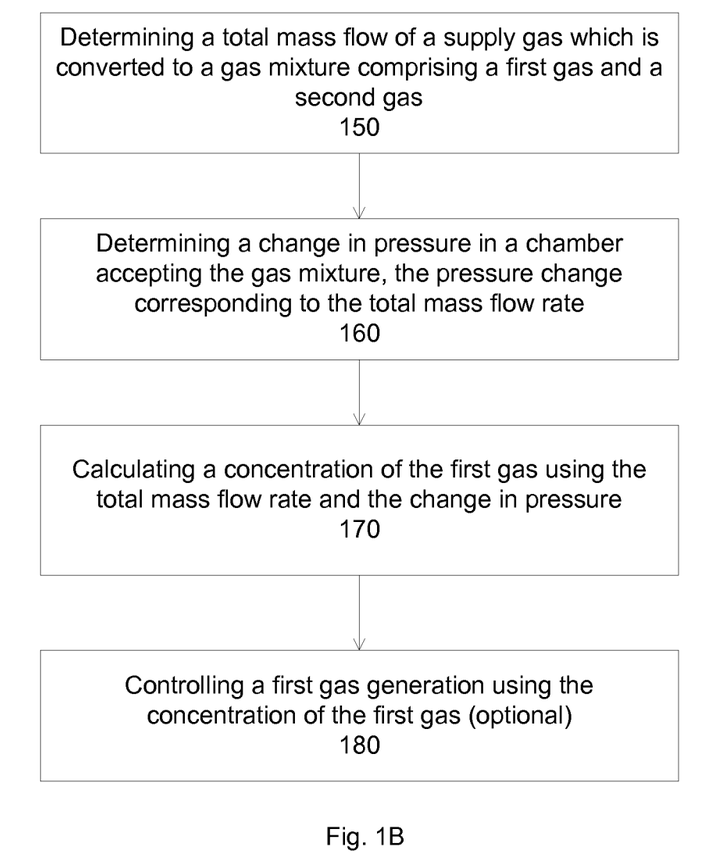
FIG. 1B illustrates another exemplary flowchart for determining individual mass flow rates or concentration in a gas mixture flow according to some embodiments of the present invention.

FIG. 1B illustrates another exemplary flowchart for determining individual mass flow rates or concentration in a gas mixture flow according to some embodiments of the present invention. Better accuracy can be achieved with calculating differential values instead of measuring absolute values. For example, calculating a chamber pressure difference can have better precision than measuring an absolute value of chamber pressure. Thus in some embodiments, the present invention employs differential measurements of mass flow and chamber pressure in determining concentration.

In operation 150, a total mass flow of a supply gas for a predetermined time is determined. In operation 160, a change in chamber pressure due to the gas mixture is measured. In operation 170, the individual mass flow rates or the concentration can be calculated using the total mass flow and the change in chamber pressure. For example, a weight percent concentration of ozone in a gas mixture of ozone and oxygen can be calculated using Eqn 5 above. In operation 180, the concentration of the first gas can be used to control a first gas generation system to achieve a desired concentration value. Other variations are also within the scope of the present invention. For example, instead of calculating concentration directly from the changes in flow and pressure, individual numbers of moles for ozone and oxygen can be determined, and the ozone concentration is calculated using Eqn 4.

In some embodiments, the present invention discloses systems and methods to determine a concentration of ozone in an ozone/oxygen mixture where the ozone is generated from a supply of oxygen gas.

Figure 2:
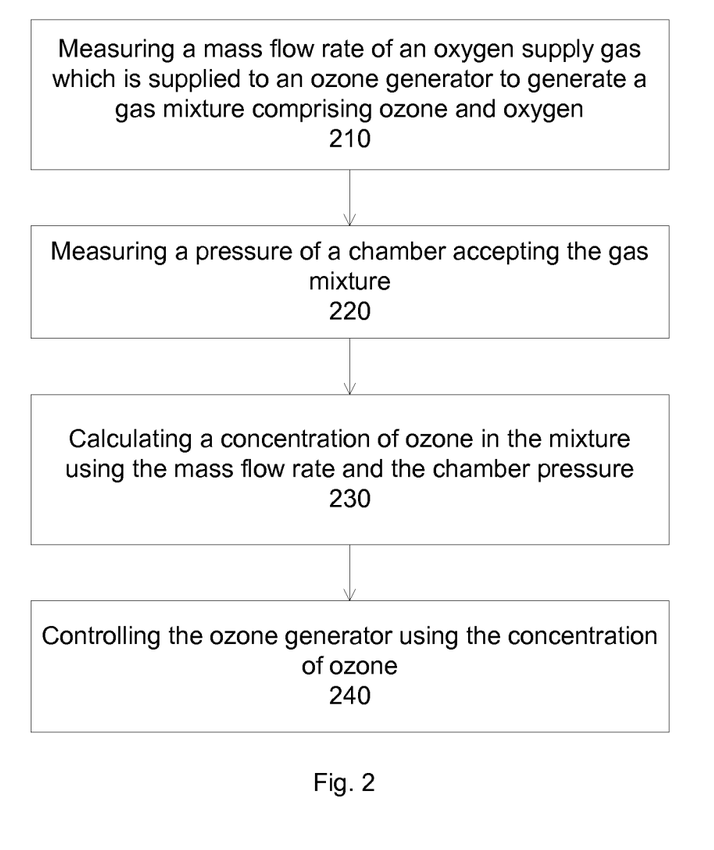
FIG. 2 illustrates an exemplary flowchart for calculating an ozone concentration in an ozone-oxygen gas mixture according to some embodiments of the present invention.

FIG. 2 illustrates an exemplary flowchart for calculating an ozone concentration in an ozone-oxygen gas mixture according to some embodiments of the present invention. In operation 210, a mass flow rate of the oxygen supply gas is determined. An ozone-oxygen mixture is generated from the oxygen supply gas, for example, through an ozone generator. Additional gases can be supplied to the ozone generator, resulting in the output gas mixture comprising the additional gases. In operation 220, the output of the ozone generator is supplied to a measured chamber, and a chamber pressure is measured. In operation 230, the ozone concentration can be calculated using the mass flow rate and the chamber pressure. Alternatively, individual mass flow rates in the gas mixture, such as ozone mass flow rate, can be calculated. In operation 240, the concentration of ozone can be used to control the ozone generator to achieve a desired or setting concentration value.

Figure 3:
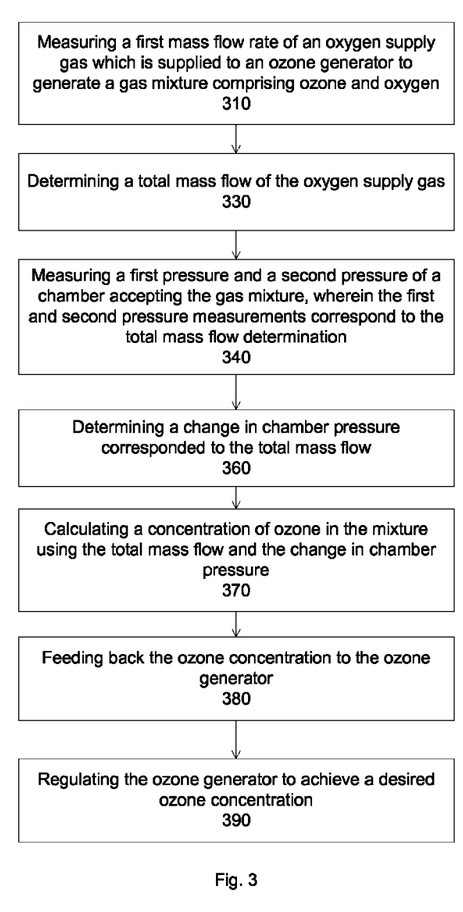
FIG. 3 illustrates another exemplary flowchart for calculating an ozone concentration generated by an ozone generator according to some embodiments of the present invention.

FIG. 3 illustrates another exemplary flowchart for calculating an ozone concentration generated by an ozone generator according to some embodiments of the present invention. The ozone generator comprises an oxygen supply gas for generating a gas mixture of ozone and oxygen, and can comprise additional gases, such as a nitrogen catalyst gas for improving ozone generation efficiency. The additional gases remain the same after passing through the ozone generator, and therefore its characteristics and effects are known and can be subtracted from the gas mixture output of the ozone generator, to allow a calculation of ozone concentration from a two-gas mixture of ozone and oxygen.

In operation 310, a mass flow rate of the oxygen supply gas is measured. In operation 330, a total mass flow of the oxygen supply gas is determined, for example, during a predetermined period. For a fixed mass flow rate, the total mass flow can be determined by multiplying the measured mass flow rate with the predetermined time. Alternatively, the total mass flow can be integrated for the predetermined period, such as by a numerical process. For example, multiple mass flow rates can be measured at small intervals, and the mass flows can be summed together to form the total mass flow.

In operation 340, a first pressure and a second pressure of a chamber accepting the gas mixture of ozone and oxygen are measured. The first and second pressure measurements correspond to the total mass flow determination, such as for the predetermined period used to calculate the total mass flow. For example, the first and second pressure measurements can be performed at the beginning and the end of the predetermined period, respectively. In operation 360, a pressure change corresponded to the total mass flow is determined, for example, by subtracting the first pressure measurement from the second pressure measurement.

In some embodiments, a total mass flow and a pressure difference due to the total mass flow are determined for the calculation of concentration. Variations of the above procedure can be used, such as using only one pressure measurement. For example, by pumping a chamber to vacuum, a first pressure value can be known (e.g., zero pressure). Then one pressure measurement is performed after a certain period with a known mass flow rate. Other techniques can also be used, for example, establishing a pressure rise curve as a function of time for a known mass flow rate.

In operation 370, individual mass flow rates or concentration can be determined from the total mass flow and the corresponding chamber pressure change. For example, ozone concentration can be calculated using the formula of Eqn 5. In operation 380, the concentration of ozone is fed back to the ozone generator. On operation 390, the power of the ozone generator is regulated based on the measured ozone concentration to achieve a desired or setting concentration value.

In some embodiments, the present invention discloses systems to measure individual flow rates or concentration in a gas mixture, such as an ozone concentration generated from an oxygen supply gas. In some embodiments, the present system comprises a flow meter and a chamber having a pressure gauge. A flow rate meter, such as a mass flow meter or a mass flow controller can be coupled to the supply gas to measure a flow rate of the supply gas. A chamber can be coupled to the gas mixture to accept the flow of the gas mixture. The chamber further comprises a pressure device, such as a pressure gauge to measure a chamber pressure.

Figure 4A:
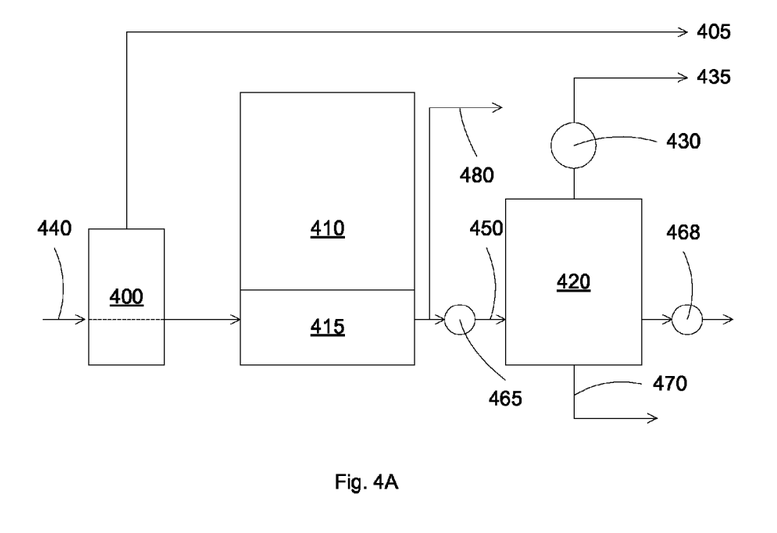
FIGS. 4A-4B illustrate exemplary system configurations for concentration determination according to some embodiments of the present invention.
Figure 4B:
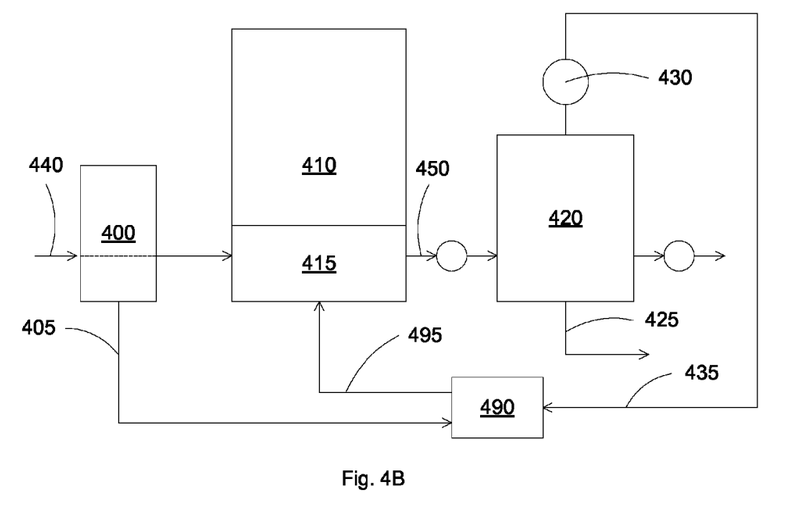

FIGS. 4A-4B illustrate exemplary system configurations for concentration determination according to some embodiments of the present invention. The following description describes a system for ozone concentration determination, but the invention is not so limited, and can be applied to any gas mixture system employing the same principles. In FIG. 4A, an ozone generator 410 accepts an oxygen input supply gas 440, and generates a gas mixture 450 of ozone and oxygen. An optional bypass line 480 can be included to divert the output gas mixture flow from the ozone generator. The ozone generator can include a power controller 415 to control the operation of the ozone generator 410, such as adjusting a power generation or regulating an input or output flow. A chamber 420 is coupled to the output 450 of the ozone generator 410, accepting the output gas mixture of ozone and oxygen generated by the ozone generator. A pressure device, such as a pressure gauge 430, is coupled to the chamber 420 to measure the chamber pressure. Optional pumping mechanism 470 can be included, to pump the chamber 420 to vacuum or to a low pressure. Optional isolation valves 465 and 468 can be included to isolate the chamber 420. For example, valves 465 and 468 can be closed during pumping. Valve 468 can be close while valve 465 open during a pressure measurement corresponded to a gas mixture flow. Valves 465 and 468 can be open during operation, for example, to deliver gas mixture to a process chamber. Pressure gauge 430 comprises an output 435, identifying the chamber pressure. A flow measurement device, such as a flow meter or controller 400, is coupled to the input oxygen supply gas 440 to measure a flow rate of the oxygen supply gas. Flow meter 400 comprises an output 405, identifying the oxygen supply flow rate. An optional controller can be included to perform the concentration calculation.

During operation, valves 465 and 468 are closed with the pumping 470 running. A first pressure of chamber 420 is measured, through the pressure gauge 430. Ozone generator 410 is running, with output diverted to the bypass line 480 to stabilize the ozone generation. Valve 465 is open, and the chamber pressure is measured again. From the changes in chamber pressure, together with the mass flow value of oxygen supply gas 440, measured through the mass flow meter 400, the concentration of ozone can be determined. Variations of the above process can be made, for example, multiple pressure measurements can be performed to provide multiple concentration values, which can allow better accuracy.

In FIG. 4B, a controller 490 is added to control the ozone concentration. The controller 490 accepts measurements 405 and 435 from mass flow meter 400 and from pressure gauge 430, respectively. The controller then calculates an ozone concentration generated by the ozone generator 410. The concentration is compared with a desired ozone concentration, and a power output 495 is sent to the ozone generator 410 to dynamically adjust the power of the ozone generator until the measured concentration matches with the setting concentration.

In some embodiments, one or more third gases can be included in the gas flow mixture, for example, to dilute the mixture or to perform some other functions. For example, an ozone generator can accept a small flow of nitrogen, in addition to the oxygen flow, to improve the performance such as the ozone generation ability. In this case, the gas flow mixture comprises ozone, oxygen and nitrogen.

In some embodiments, the present invention discloses systems and methods to measure and control individual gas flow rates or concentrations in a gas flow mixture comprising more than two gases. In some embodiments, the process is performed by removing the effects of the third gases, effectively reducing the multiple-gas mixture system into a two-gas mixture system. In other embodiments, a comprehensive calculation can be used, setting and solving a system of linear equations involving all gases. The present description describes some approaches, but variations are also within the scope of the present invention.

In some embodiments, the present invention discloses methods to determine a concentration of a first gas in a gas mixture comprising the first gas and a second gas. An exemplary method comprises measuring a total mass flow of a supply gas wherein the supply gas is converted to the gas mixture; measuring a corresponding change in pressure of a chamber accepting the gas mixture; and calculating a concentration of the first gas using the total mass flow and the change in pressure. In some embodiments, the method determines the concentration of ozone in a mixture of ozone and oxygen with the first gas comprising ozone, the second gas comprising oxygen and the supply gas comprising oxygen.

In some embodiments, determining a total mass flow rate can comprise measuring a mass flow rate of the oxygen supply gas; and calculating a total mass flow rate of the oxygen supply gas during a predetermined period. Further, determining a change in a chamber pressure can comprise measuring a first chamber pressure corresponding to a beginning of the predetermined period; measuring a second chamber pressure corresponding to an end of the predetermined period; and calculating a change of chamber pressure.

In some embodiments where the mixture further comprises a nitrogen gas with known flow rate, the method can further comprise calculating a change of chamber pressure due to ozone and oxygen by subtracting the effect of the nitrogen gas.

In some embodiments, the present invention discloses a method to control a desired concentration comprising delivering a signal representing the determined concentration of the first gas to one of a first gas generation; and regulating the one of a first gas generation and a second gas generation to achieve a desired concentration based on the signal. The control method can regulate the generation of ozone from oxygen with the first gas comprising ozone, and the second gas comprising oxygen.

Figure 5:
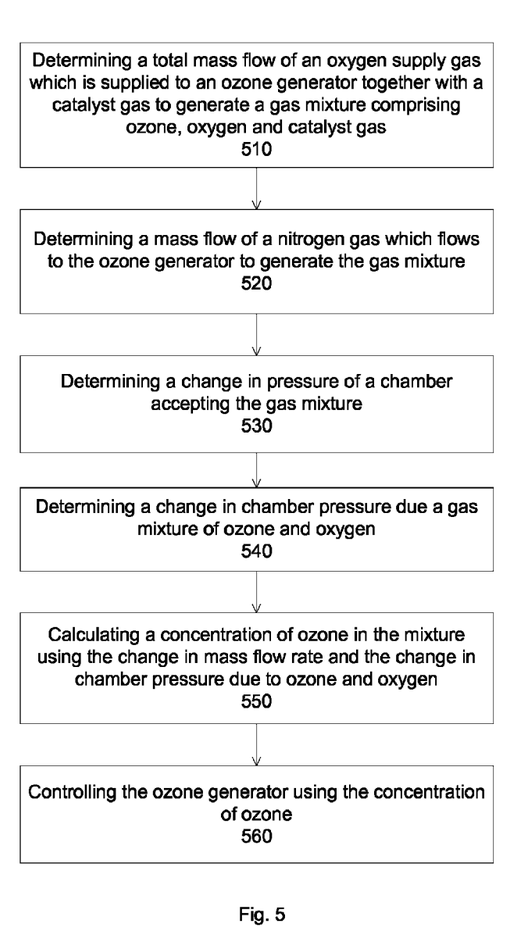
FIG. 5 illustrates an exemplary flowchart for determining individual mass flow rates or concentration in a multiple-gas mixture flow according to some embodiments of the present invention.

FIG. 5 illustrates an exemplary flowchart for determining individual mass flow rates or concentration in a multiple-gas mixture flow according to some embodiments of the present invention. The process is described using an ozone generator with oxygen supply gas, but other systems can be used. The ozone generator accepts oxygen and nitrogen catalyst as inputs, and supplies a multiple-gas mixture comprising ozone, oxygen, and nitrogen.

In operation 510, a total mass flow of the oxygen supply gas is determined, for example, through a mass flow meter coupled to the oxygen supply gas. The total mass flow can also be determined from a measurement of both oxygen and nitrogen input supply, in which the nitrogen gas flow is subtracted. In operation 520, a mass flow of nitrogen is determined.

In operation 530, a pressure change of a chamber corresponding to the total mass flow is determined, for example, by measuring the pressure change before and after the oxygen supply gas flows.

In operation 540, a pressure change due to the gas mixture of ozone and oxygen is determined, for example, by subtracting the effects of the nitrogen gas. The Ideal gas law can be used, linking the mass of nitrogen to the partial pressure in the chamber due to nitrogen alone. In operation 550, ozone concentration is calculated. With the total mass flow of oxygen supply gas, together with the pressure change due to oxygen and ozone, calculations based on a two-gas mixture system can be performed, using any process described above, to determine the ozone concentration.

In operation 560, the power of the ozone generator is regulated based on the measured ozone concentration to achieve a desired concentration value.

Figure 6A:
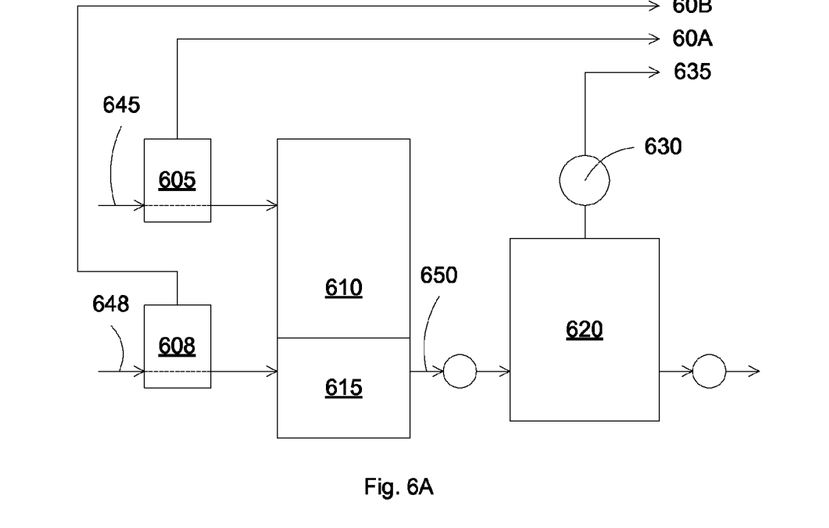
FIGS. 6A-6B illustrate exemplary multiple-gas mixture system configurations for concentration determination according to some embodiments of the present invention.
Figure 6B:
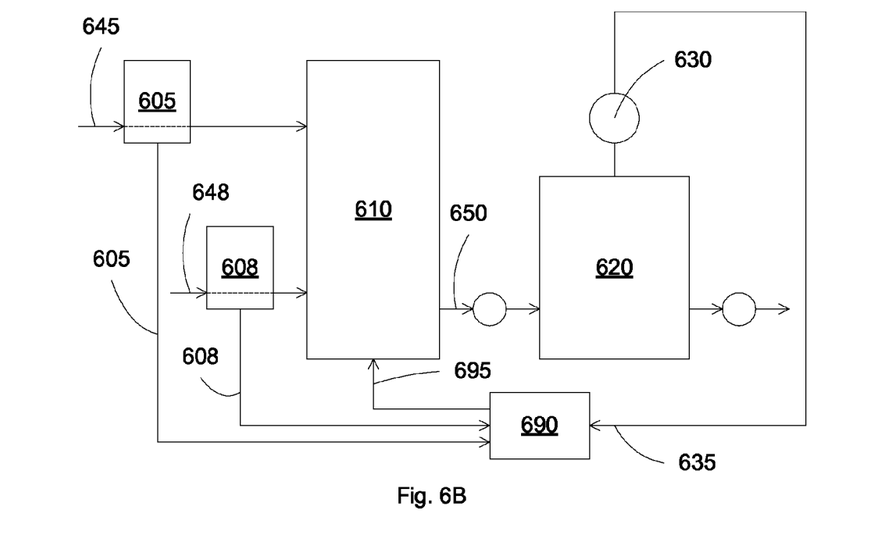

FIGS. 6A-6B illustrate exemplary multiple-gas mixture system configurations for concentration determination according to some embodiments of the present invention. In FIG. 6A, an ozone generator 610 accepts an oxygen input supply gas 645 and a nitrogen catalyst input supply gas 648, and generates a gas mixture 650 of ozone, oxygen, and nitrogen. An optional bypass line can be included to divert the output gas mixture flow from the ozone generator. The ozone generator can include a power controller 615 to control the operation of the ozone generator 610, such as adjusting a power generation or regulating an input or output flow. A chamber 620 is coupled to the output 650 of the ozone generator 610, accepting the output gas mixture of ozone, oxygen, and nitrogen generated by the ozone generator. A pressure device, such as a pressure gauge 630, is coupled to the chamber 620 to measure the chamber pressure. Optional pumping mechanism can be included, to pump the chamber to vacuum or to a low pressure. Optional isolation valves can be included to isolate the chamber 620. Pressure gauge 630 comprises an output 635, identifying the chamber pressure. Flow measurement devices, such as flow meters or controllers 605 and 608, are coupled to the input oxygen and nitrogen supply gases 645 and 648 to measure a flow rate of the oxygen and nitrogen supply gases, respectively. Flow meters 605 and 608 comprise outputs 605 and 608, identifying the oxygen and nitrogen supply flow rates. An optional controller can be included to perform the concentration calculation, based on the measurement 605, 608, and 635.

In FIG. 6B, a controller 690 is added to control the ozone concentration. The controller 690 accepts measurements 605, 608 and 635 from mass flow meters 605 and 608, and from pressure gauge 630, respectively. The controller then calculates an ozone concentration generated by the ozone generator 610. The concentration is compared with a desired or setting ozone concentration, and a power output 695 is sent to the ozone generator 610 to dynamically adjust the power of the ozone generator until the measured concentration matches with the setting concentration.

In some embodiments, the present invention discloses an ozone sensor that can operate at a wide pressure range, such as the pressure ranges suitable to conventional mass flow meters or controllers. In addition, the present systems can measure ozone concentration at low pressure ranges, such as less than 400 Torr, preferably less than 100 Torr, and more preferably less than 10 Torr. This low pressure operation offers significant advantages over prior art ozone sensors, which typically can perform measurements at pressures higher than 400 Torr. For example, existing ozone sensors are based on infrared absorption, and thus require a minimum amount of ozone molecules to have measurable absorption signals.

In some embodiments, the present invention discloses an ozone sensor capable to connecting to a vacuum processing chamber where the operating pressure is less than a few hundred Torr, and typically less than a few Torr. The present ozone sensor can be installed at point of use to enable measuring or monitor the level of ozone in a process chamber.

In some embodiments, the present invention discloses gas concentration sensors to determine a concentration of a first gas in a gas mixture comprising the first gas and a second gas. An exemplary gas concentration sensor comprises a mass flow meter to measure a mass flow rate of a supply gas which is converted to the gas mixture; a chamber accepting the mixture flow; a pressure gauge coupled to the chamber to measure a pressure of the chamber; and a controller coupled to an output of the mass flow meter and an output of the pressure gauge, the controller configured to produce a signal related to the concentration of the first gas based on a mass flow rate and a pressure change. The gas concentration sensor can further comprise isolation and pumping mechanism coupled to the chamber to permit a pressure change determination.

In some embodiments, the gas concentration sensor can determine the concentration of ozone in a mixture of ozone and oxygen, with the first gas comprising ozone, and the second gas comprising oxygen. The mass flow meter can measure the flow rate of oxygen. The gas mixture can further comprise nitrogen with a known flow rate; and the controller can be further configured to calculate the pressure change due to ozone and oxygen from the pressure change due to the total gas mixture.

In some embodiments, the gas concentration sensor can further comprise a feedback circuit to provide the concentration signal to an ozone generator; and a power output based on a difference between the concentration signal and a desired concentration to regulate the ozone generator.

In some embodiments, the present invention discloses a processing system which comprises a gas concentration sensor and further comprises a vacuum process chamber, wherein the outlet port for the gas mixture flow is disposed in a vicinity of the vacuum process chamber. The controller can be further coupled to the vacuum process chamber to operate the vacuum process chamber.

Figure 7:
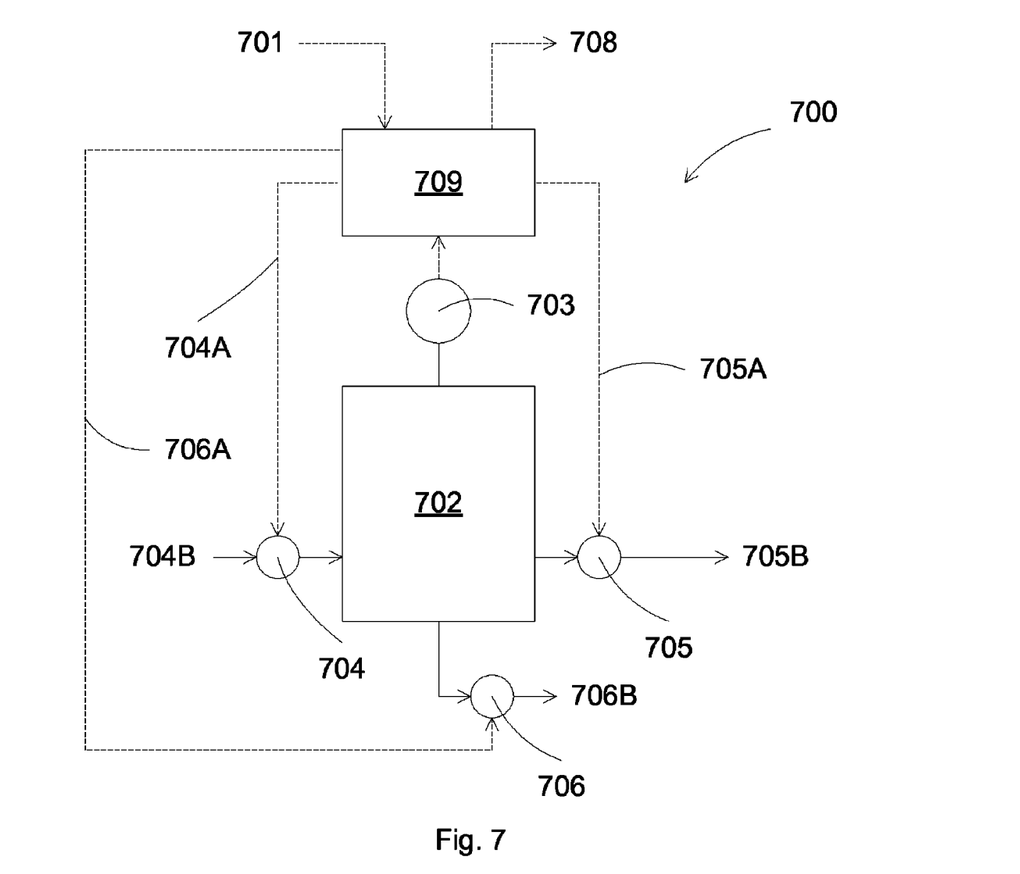
FIG. 7 illustrates an exemplary ozone sensor according to some embodiments of the present invention.

FIG. 7 illustrates an exemplary ozone sensor according to some embodiments of the present invention. The ozone sensor 700 comprises a chamber 702 coupled to a pressure gauge 703. The chamber 702 comprises openings 704B, 705B, and 706B, for coupling with an ozone input, an output, and a pumping system, respectively. The output opening 705B can be optional, designed to allow ozone to pass through the ozone sensor while being measured. The ozone sensor can be coupled to a dead end branch, e.g., without any output, to simply measure the ozone concentration. The pumping opening 706B can also be optional, designed to evacuate the chamber 702. For example, opening 704B can be used to both accepting ozone input and pumping line, preferably through a valve manifold.

The openings 704B, 705B, and 706B are coupled to valves 704, 705 and 706, respectively, for controlling the openings. The valves are preferably controllable, for example, through a controller 709, to allow automatic operation. For example, the controller 709 can open valve 706 for pumping, then open valve 704 for accepting an ozone flow for measurement.

The controller also accepts an output from pressure gauge 703, together with one or more external mass flow inputs 701, which can be used to calculate the ozone concentration according to any of the embodiments described above. The controller can have an output 708, providing the ozone concentration value. The controller 709 also comprises programming to automatically operate the valves and the measurements, together with algorithm to determine the ozone concentration.

The accuracy of the ozone concentration measurement depends on the pressure gauge and the mass flow readings. High accuracy can be obtained with high quality pressure gauge and mass flow meter. For example, pressure gauges can be accurate at 0.05% of the maximum pressure setting, thus by selecting a proper pressure gauge, high accuracy ozone concentration measurements can be performed. The present ozone sensor can performed at any pressure setting, for example, at low pressure of a few Torr and a high pressure of atmospheric and above.

In some embodiments, the present invention discloses an ozone sensor that can operate at a wide pressure range, such as the pressure ranges suitable to conventional mass flow meters or controllers. In addition, the present systems can measure ozone concentration at low pressure ranges, such as less than 400 Torr, preferably less than 100 Torr, and more preferably less than 10 Torr. This low pressure operation offers significant advantages over prior art ozone sensors, which typically can perform measurements at pressures higher than 400 Torr. For example, existing ozone sensors are based on infrared absorption, and thus require a minimum amount of ozone molecules to have measurable absorption signals.

In some embodiments, the present invention discloses an ozone sensor capable to connecting to a vacuum processing chamber where the operating pressure is less than a few hundred Torr, and typically less than a few Torr. The present ozone sensor can be installed at point of use to enable measuring or monitor the level of ozone in a process chamber.

In some embodiments, the present invention discloses a process chamber utilizing the present ozone sensor. The process chamber can be configured for application using ozone, such as TEOS/Ozone deposition, or ALD processes. Many ALD systems use ozone as an oxidant for film deposition, such as $Al_2O_3$, $HfO_2$, $ZrO_2$, $Ta_2O_5$ and $TiO_2$. Because of its quick decay characteristics, ozone cannot be stored and transported long distance, and must therefore be produced on site. Even so, the ozone generator usually is located far away from the process chamber, and the ozone concentration is measured at ozone generator output. The long delivery line, which can be heated, can affect the ozone concentration, for example, some ozone could be lost before reaching process chamber. Measuring, monitoring or controlling the ozone concentration at a point of use is therefore important for critical process control.

In some embodiments, the present invention discloses hardware and process monitoring, troubleshooting as well as controlling, comprising positioning an ozone sensor in a close vicinity of a process chamber, and configuring the system controller to accept the operation of the ozone sensor.

Figure 8A:
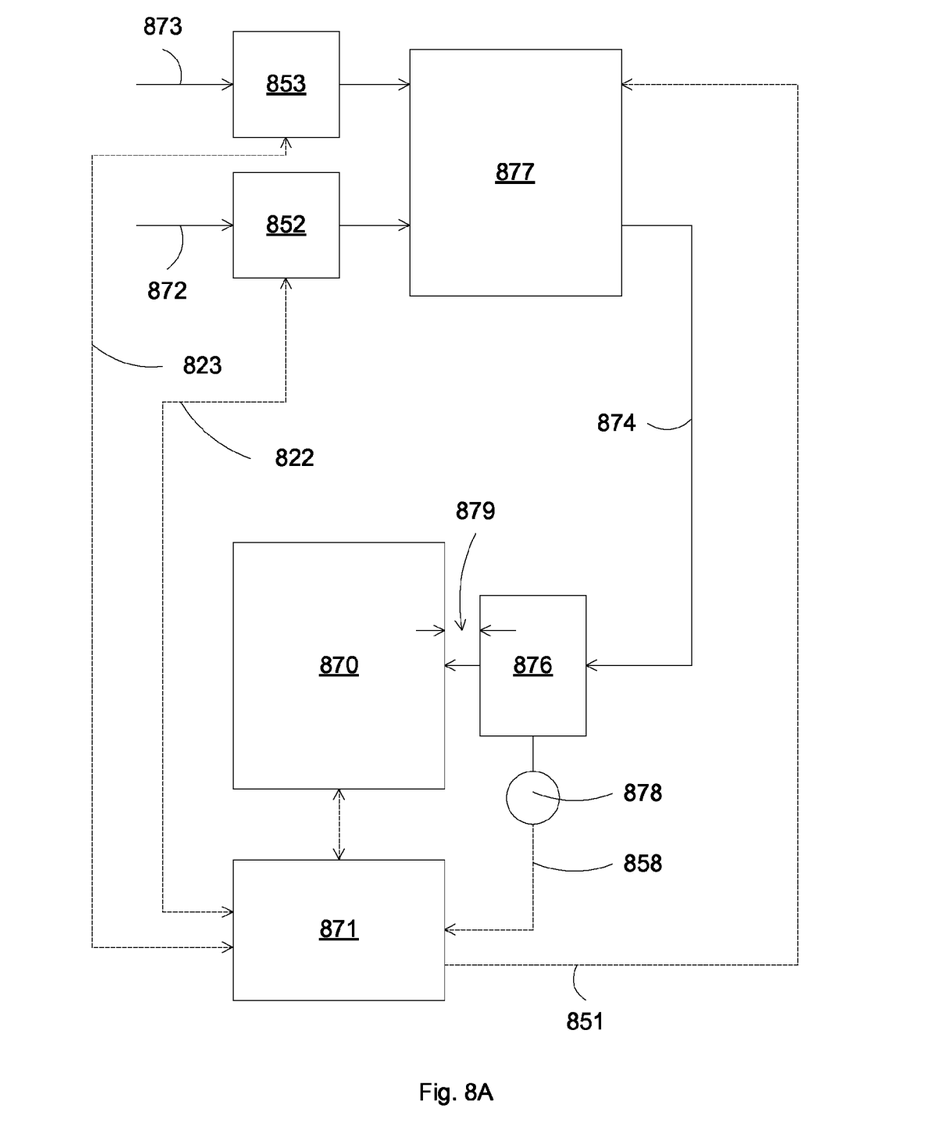
FIGS. 8A-8B illustrate exemplary configurations for a process chamber utilizing an ozone measurement according to some embodiments of the present invention.
Figure 8B:
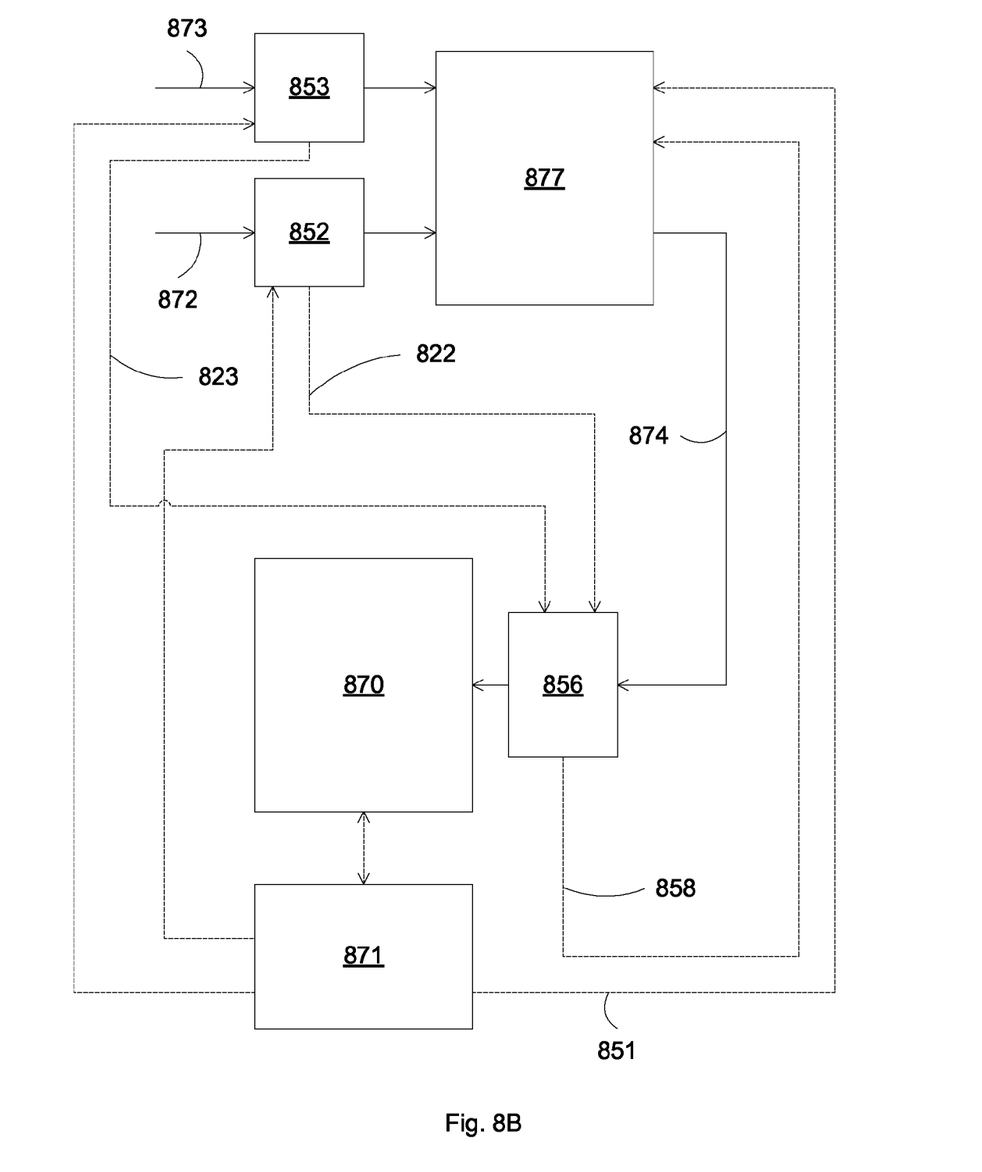

FIGS. 8A-8B illustrate exemplary configurations for a process chamber utilizing an ozone sensor according to some embodiments of the present invention. In FIG. 8A, separate components are put together for measuring ozone concentration. A process chamber 870 is controlled by a system controller 871, for example, to heat a substrate support, to transfer substrates in and out of the process chamber, or to control process gases and pressure in the process chamber. An ozone generator 877 accepts an oxygen input flow 872 and a nitrogen input flow 873, and outputs an ozone mixture 874 (e.g., a mixture of oxygen, ozone and nitrogen) to the process chamber. A chamber 876 is positioned in the path of the ozone mixture 874, in the vicinity of the process chamber. The distance 879 between the chamber 876 and the process chamber 870 is preferably short to provide point of use measurement and controlling. Typically, the distance 879 is preferably less than 1 m, and more preferably less than 10 cm from the process chamber. At that distance, the chamber 876 measuring ozone concentration will have an operating pressure determined by the process chamber, and thus for vacuum processing, the present ozone concentration measurement can be used, since it can operate at low pressure conditions.

The chamber 876 includes a pressure gauge, such as a pressure transducer 878 to provide pressure measurements of the chamber 876. In some embodiments, the ozone sensor can be a conventional mass flow meter or controller, and the system configuration and software can be modified to provide measuring and controlling capability. The output 858 of the pressure gauge 878 is supplied to the system controller 871, together with the oxygen flow 822 measured from flow controller 852 and the nitrogen flow 853 measured from flow controller 823. The system controller 871 can calculate the ozone concentration based on these inputs. The controller can output a power signal 851 to the ozone generator 877 to regulate the ozone concentration, matching the ozone measurement with a desired ozone level. The system controller 871 can also control the flow rates of oxygen and nitrogen, through outputs to the flow controller 852 and 853.

In FIG. 8B, an ozone sensor 856, such as the ozone sensor 700 described in FIG. 7 is used for measuring ozone concentration. The ozone sensor can receive the oxygen flow 822 measured from flow controller 852 and the nitrogen flow 823 measured from flow controller 853, and outputs an ozone concentration signal 858 back to the ozone generator for regulating the ozone concentration. The system controller 871 can output a desired ozone concentration to the ozone generator 877 to automatically adjust the power of the ozone generator 877 to regulate the ozone concentration, matching the ozone measurement with a desired ozone level. The system controller 871 can optionally control the flow rates of oxygen and nitrogen, through outputs to the flow controller 852 and 853.

In some embodiments, the present invention discloses methods to configure a vacuum process chamber utilizing ozone generated from an ozone generator accepting an oxygen flow. An exemplary method comprises installing a chamber in fluid communication with the vacuum process chamber; coupling a pressure output from a pressure gauge measuring a pressure in the chamber to a system controller; coupling an output flow from the ozone generator accepting an oxygen input flow to the chamber; coupling an oxygen flow output measuring the oxygen input flow to the system controller; and programming the system controller to calculate an ozone concentration from a change in the pressure output and the oxygen flow output. The method can further comprise programming the system controller to output a power signal to the ozone generator to achieve a desired ozone concentration.

In some embodiments where the ozone generator further accepts a catalyst flow, such as a nitrogen flow, the method further comprises coupling a nitrogen flow output measuring the nitrogen flow to the system controller; and programming the system controller to calculate a change in pressure output due to ozone and oxygen. The vacuum process chamber can be configured to perform a deposition utilizing ozone as a process gas, wherein the deposition comprising at least one of atomic layer deposition and chemical vapor deposition.

Figure 9:
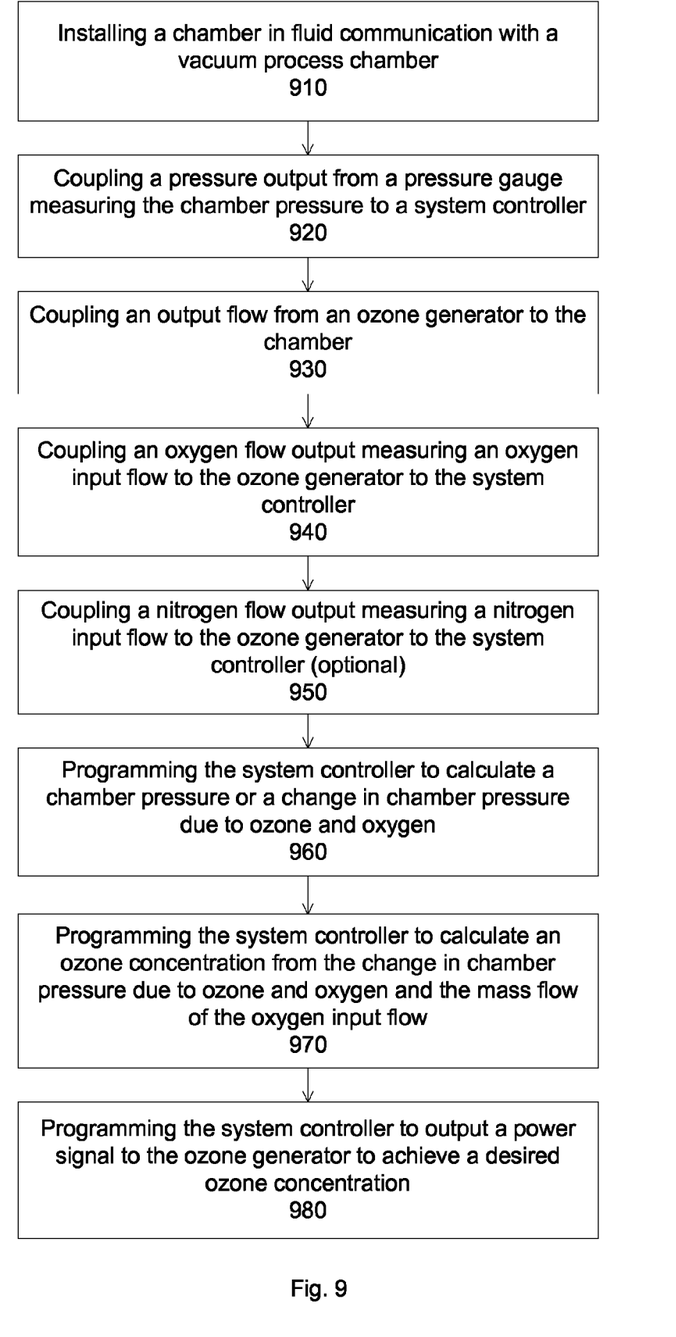
FIG. 9 illustrates an exemplary flowchart for configuring a system using an ozone sensor according to some embodiments of the present invention.

FIG. 9 illustrates an exemplary flowchart for configuring a system using an ozone sensor according to some embodiments of the present invention. The flowchart describes the installation of the ozone system as shown in FIG. 8A, the invention is not so limited, and also includes variations, such as for system shown in FIG. 8B. In operation 910, a chamber is installed, in fluid communication with a vacuum process chamber. In operation 920, a pressure output from a pressure gauge measuring the chamber pressure is coupled to a system controller. In operation 930, an output flow from an ozone generator is coupled to the chamber. In operation 940, an oxygen flow output measuring an oxygen input flow to the ozone generator is coupled to the system controller. In operation 950, a nitrogen flow output measuring a nitrogen input flow to the ozone generator is coupled to the system controller. This operation is optional, and is performed only for ozone generators with catalyst flow. In operation 960, the system controller is programmed to calculate a chamber pressure or a change in chamber pressure due to ozone and oxygen. For example, without catalyst flows, the measured chamber pressure is due to the mixture of ozone and oxygen. With a nitrogen catalyst flow, the measured pressure also includes a partial pressure due to nitrogen, and therefore the nitrogen partial pressure is needed to be subtracted from the total pressure measurement to obtain a pressure value due to ozone and oxygen. In operation 970, the system controller is programmed to calculate an ozone concentration from the change in chamber pressure due to ozone and oxygen and the mass flow of the oxygen input flow. The controller programming can be combined. For example, the system controller can comprise a software programming for operating the process chamber, and the ozone concentration calculation is included in the software programming. In operation 980, the system controller is programmed to output a power signal to the ozone generator to achieve a desired ozone concentration.

Although the foregoing examples have been described in some detail for purposes of clarity of understanding, the invention is not limited to the details provided. There are many alternative ways of implementing the invention. The disclosed examples are illustrative and not restrictive.

What is claimed is:

1. A method to determine a concentration of a first gas in a gas mixture, the gas mixture comprising the first gas and a second gas, the method comprising:
measuring a mass flow rate of a supply gas;
converting the supply gas to the gas mixture, wherein a total mass flow rate of the gas mixture is equal to the mass flow rate of the supply gas;
calculating a rate of change in pressure of a chamber accepting the gas mixture, the rate of change in pressure corresponding to the total mass flow rate the gas mixture; and
calculating a concentration (C (wt %)) of the first gas in the gas mixture using the total mass flow rate of the gas mixture and the rate of change in pressure of the chamber using $$C(\text{wt \%}) = \frac{M_{O2}\left(\Delta F - M_{O2}\Delta P \frac{V}{RT}\right)}{\Delta F(M_{O2} - M_{O3})}$$

where $M_{O2}$ and $M_{O3}$ are the mass of oxygen and mass of ozone respectively, $\Delta P$ is the change in pressure, $\Delta F$ is the change in mass flow, V is the volume, T is the temperature, and R is the gas constant; and wherein the first gas comprises ozone, and the second gas comprises oxygen, wherein the method determines a concentration of ozone in a gas mixture of ozone and oxygen.

2. A method as in claim 1 wherein calculating the rate of change in pressure comprises:
measuring a first pressure corresponding to a beginning of a time period;
measuring a second pressure corresponding to an end of the time period;
calculating the rate of change in pressure.

3. A method as in claim 1 wherein the gas mixture further comprises a nitrogen gas with known mass flow rate, the method further comprising:
calculating a rate of change in pressure due to the ozone and oxygen gas mixture by subtracting the effect of the nitrogen gas.

4. A method to control a desired concentration using a concentration determination method as in claim 1, the method further comprising:
delivering a signal representing the concentration of the first gas to a first gas generator;
regulating the first gas generator to achieve the desired concentration based on the signal.

5. A method as in claim 4 wherein the first gas comprises ozone, and the second gas comprises oxygen, the method regulates the generation of ozone from oxygen.

6. A gas concentration sensor to determine a concentration of a first gas in a gas mixture, the gas mixture comprising the first gas and a second gas, the gas concentration sensor comprising:
a mass flow meter to measure a mass flow rate of a supply gas;
an ozone generator to convert the supply gas to the gas mixture, wherein a total mass flow rate of the gas mixture is equal to the mass flow rate of the supply gas;
a chamber accepting a flow of the gas mixture;
a pressure gauge coupled to the chamber to measure a pressure of the chamber; and a controller coupled to an output of the mass flow meter and an output of the pressure gauge, the controller configured to produce a concentration signal related to the concentration of the first gas based on the total mass flow rate and the rate of change in pressure corresponding to the total mass flow rate,
wherein the first gas comprises ozone, and the second gas comprises oxygen;
a feedback circuit to provide the concentration signal to the ozone generator; and
a power output based on a difference between the concentration signal and a desired concentration to regulate the ozone generator.

7. A gas concentration sensor as in claim 6 further comprising
an isolating and pumping mechanism coupled to the chamber.

8. A gas concentration sensor as in claim 6 wherein the mass flow meter measures the mass flow rate of oxygen before the oxygen is converted to a mixture of ozone and oxygen.

9. A gas concentration sensor as in claim 6 wherein the gas mixture further comprises nitrogen gas with a known mass flow rate; and wherein the controller is further configured to calculate a rate of change in pressure due to ozone and oxygen from the rate of change in pressure due to the gas mixture by subtracting the effect of the nitrogen gas.

10. A processing system comprising a gas concentration sensor as in claim 6 and further comprising a process chamber, wherein an outlet port of the gas concentration sensor is disposed in a vicinity of an input of the process chamber.

11. A processing system as in claim 10, wherein the controller is further coupled to the process chamber to operate the process chamber.

12. A method to configure a process chamber for utilizing ozone generated from an ozone generator, the method comprising:
installing a chamber in fluid communication with the process chamber;
measuring a pressure in the chamber and providing a pressure output signal to a system controller;
coupling an output flow from the ozone generator to the chamber;
measuring an oxygen input mass flow rate to the ozone generator and providing an oxygen input mass flow rate signal to the system controller;
programming the system controller to calculate an ozone concentration from the pressure output signal and the oxygen input mass flow rate signal.

13. A method as in claim 12 further comprising
programming the system controller to output a power signal to the ozone generator to regulate the ozone generator.

14. A method as in claim 12 wherein the ozone generator further accepts a nitrogen gas flow, the method further comprising:
measuring the nitrogen gas mass flow rate and providing a nitrogen gas mass flow rate signal to the system controller; and
programming the system controller to calculate a pressure due to ozone and oxygen by subtracting the effect of the nitrogen gas.

15. A method as in claim 12 wherein the process chamber is configured to perform a deposition utilizing ozone as a process gas, wherein the deposition comprises at least one of atomic layer deposition and chemical vapor deposition.

* * * * *